United States Patent
Arvindan et al.

(10) Patent No.: US 12,235,264 B2
(45) Date of Patent: Feb. 25, 2025

(54) ENHANCED CYTOMETRY FOR TISSUE CHARACTERIZATION AND SCREENING

(71) Applicant: FIVE PRIME THERAPEUTICS, INC., South San Francisco, CA (US)

(72) Inventors: Nallakkan Arvindan, Moraga, CA (US); Stephen Mehi, San Francisco, CA (US); Guanqing Ou, South San Francisco, CA (US)

(73) Assignee: FIVE PRIME THERAPEUTICS, INC., South San Francisco, CA (US)

( * ) Notice: Subject to any disclaimer, the term of this patent is extended or adjusted under 35 U.S.C. 154(b) by 1087 days.

(21) Appl. No.: 17/058,108

(22) PCT Filed: May 23, 2019

(86) PCT No.: PCT/US2019/033755
§ 371 (c)(1),
(2) Date: Nov. 23, 2020

(87) PCT Pub. No.: WO2019/226897
PCT Pub. Date: Nov. 28, 2019

(65) Prior Publication Data
US 2021/0215687 A1    Jul. 15, 2021

Related U.S. Application Data

(60) Provisional application No. 62/676,620, filed on May 25, 2018.

(51) Int. Cl.
*G01N 33/543* (2006.01)
*B01F 23/50* (2022.01)
(Continued)

(52) U.S. Cl.
CPC ....... *G01N 33/54366* (2013.01); *B01F 23/50* (2022.01); *G02B 13/22* (2013.01);
(Continued)

(58) Field of Classification Search
CPC ............ C12Q 1/6841; C12Q 2563/107; C12Q 2565/601; C12Q 2565/629;
(Continued)

(56) References Cited

U.S. PATENT DOCUMENTS

| 10,168,525 B2 | 1/2019 | Kim et al. |
| 2002/0159162 A1* | 10/2002 | Ramm ................... G02B 13/14 359/663 |

(Continued)

FOREIGN PATENT DOCUMENTS

| EP | 2 148 187 A1 | 1/2010 |
| JP | 2008-224465 A | 9/2008 |

(Continued)

OTHER PUBLICATIONS

Chinese Patent Application No. 201980030877.6, Office Action and Search Report, dated May 25, 2023.
(Continued)

*Primary Examiner* — Jennifer Wecker
*Assistant Examiner* — Jonathan Bortoli
(74) *Attorney, Agent, or Firm* — MARSHALL, GERSTEIN & BORUN LLP

(57) ABSTRACT

An optical imaging system (100) includes a frame (102) designed to provide mechanical coupling between a first stage (104) and a second stage (106), a sample holding region (108) located on the first stage (104), a lens arrangement, and a sensor array. The lens arrangement is disposed between the first stage (104) and the second stage (106) and is designed to receive light from a sample at the sample holding region (108) on the first stage. The lens arrangement has a numerical aperture less than 0.1. The sensor array is coupled to the second stage (106) and is designed to receive light passing through the lens arrangement.

19 Claims, 11 Drawing Sheets

(51) Int. Cl.
| | |
|---|---|
| *G02B 13/22* | (2006.01) |
| *G02B 15/00* | (2006.01) |
| *G02B 21/00* | (2006.01) |
| *G02B 21/16* | (2006.01) |
| *G02B 21/26* | (2006.01) |

(52) U.S. Cl.
CPC ......... *G02B 15/00* (2013.01); *G02B 21/0088* (2013.01); *G02B 21/16* (2013.01); *G02B 21/26* (2013.01); *B01J 2219/00351* (2013.01); *B01J 2219/00418* (2013.01)

(58) Field of Classification Search
CPC .............. G01N 33/54366; G02B 13/22; G02B 21/0088; G02B 21/16; G02B 21/24; G02B 21/26; G02B 15/00; A61K 38/39; A61K 47/08; A61K 47/10; A61P 3/04; B01F 23/50; B01J 2219/00351; B01J 2219/00418; H04L 45/64; H04W 24/00; H04W 28/0236; H04W 28/0278; H04W 28/06; H04W 28/20
See application file for complete search history.

(56) References Cited

U.S. PATENT DOCUMENTS

| | | | | |
|---|---|---|---|---|
| 2003/0151735 | A1* | 8/2003 | Blumenfeld | G01N 21/6428 356/73 |
| 2010/0019157 | A1* | 1/2010 | Furlan | G01N 21/6452 250/363.01 |
| 2015/0323462 | A1 | 11/2015 | Ghosh et al. | |
| 2016/0216503 | A1* | 7/2016 | Kim | G02B 13/0095 |

FOREIGN PATENT DOCUMENTS

| | | | |
|---|---|---|---|
| JP | 2009-015047 | A | 1/2009 |
| JP | 2010-032513 | A | 2/2010 |
| JP | 2013-150567 | A | 8/2013 |
| JP | 2017-049069 | A | 3/2017 |
| JP | 2018-504628 | A | 2/2018 |

OTHER PUBLICATIONS

Wittig et al., A reusable microfluidic plate with alternate-choice architecture for assessing growth preference in tissue culture, J. Neurosci. Methods, 144(1):79-89 (2005).
Ciftlik et al., Microfluidic processor allows rapid HER2 immunohistochemistry of breast carcinomas and signficantly reudces ambiguous (2+) read-outs, Proc. Natl. Acad. Sci., 110(14):5363-8 (2013).
European Patent Application No. 19730072, Examination Report, dated Jun. 6, 2023.
Written Opinion and International Search Report from International Application No. PCT/US2019/033755, dated Nov. 29, 2019, 20 pages.
Japanese Patent Application No. 2020-563650, Notice of Reasons for Refusal, mailed Feb. 22, 2023.
Boute, N., et al., "NanoLuc Luciferase—A Multifunctional Tool for High Throughput Antibody Screening," *Frontiers in Pharmacology*, vol. 7, Article 27, Feb. 18, 2016; 11 pages.
"ChipCytometry," Canopy Biosciences website, accessed Sep. 3, 2021, at https://info.canopybiosciences.com/chip-cytometry; 9 pages.
"Centrifuge-Free Next-Generation Cell Washing," Curiox Bio Systems website, accessed Sep. 3, 2021 at http://www.curiox.com; 7 pages.
"X-Cite mini+ Compact, LED Illumination System," Excelitas Technologies Corp. website, accessed Sep. 3, 2021 at https://www.excelitas.com/product/x-cite-mini-compact-led-illumination-system; 2 pages.
"The Maxpar Direct Immune Profiling System," Fluidigm Corporation flyer, 2019, downloaded Sep. 3, 2021 at https://www.fluidigm.com/singlearticles/maxpar-direct-immune-profiling-assay; 4 pages.
"Multiplexed Tissue Imaging Platform," GE Research website, accessed Sep. 3, 2021 at https://www.ge.com/research/project/multiplexed-tissue-imaging-platform; 2 pages.
Giesen, C., et al., "Highly multiplexed imaging of tumortissues with subcellular resolution by mass cytometry," *Nature Methods*, vol. 11, No. 4, Apr. 2014; pp. 417-422 and three additional supplemental information pages (9 total pages).
"ImagEM X2 EM-CCD camera C9100-23B," Hamamatsu Photonics K.K. website, accessed Sep. 3, 2021 at https://www.hamamatsu.com/us/en/product/type/C9100-23B/index.html; 6 pages.
"NIST Traceable Luminometer Reference Microplate," Harta Instruments website, accessed Sep. 3, 2021 at http://www.hartainstruments.com/refplate.html; 1 page.
"On-chip Sort," On-chip Biotechnologies Co., Ltd. Corporation website, accessed Sep. 3, 2021 at https://on-chipbio.com/; 11 pages.
"Microfluidic Cell Sorter: On-chip Sort," On-chip Biotechnologies Co., Ltd. Corporation website, accessed Sep. 3, 2021 at https://on-chipbio.com/product-onchip_sort/; 8 pages.
"LV200 Bioluminescence Imaging System: Overview," Olympus Corporation website, accessed Sep. 3, 2021 at https://www.olympus-lifescience.com/en/microscopes/inverted/lv200/; 6 pages.
"LV200 Bioluminescence Imaging System: Specifications," Olympus Corporation website, accessed Sep. 3, 2021 at https://www.olympus-lifescience.com/en/microscopes/inverted/lv200/; 2 pages.
"On-chip Sort," PHC Corporation website, accessed Sep. 3, 2021 at https://www.phchd.com/global/biomedical/on-chip-sort; 7 pages.
Riching, K., et al., "Quantitative Live-Cell Kinetic Degradation and Mechanistic Profiling ofPROTAC Mode of Action," *ACS Chemical Biology*, 13, Aug. 23, 2018; pp. 2758-2770.
Moreira, N.M., et al., "Imaging strategies for bio inspired materials," *Bioinspired Materials for Medical Applications*, 2017; pp. 215-239.
Gu, Biomedical engineering planning textbook of national ordinary institutes of higher learning, Biomedical Engineering Technology, Beijing: Chinese Medical Science and Technology Press (Jul. 2017).
Chinese Application No. 20198003087.6, Rejection Decision, dated Aug. 30, 2024.

\* cited by examiner

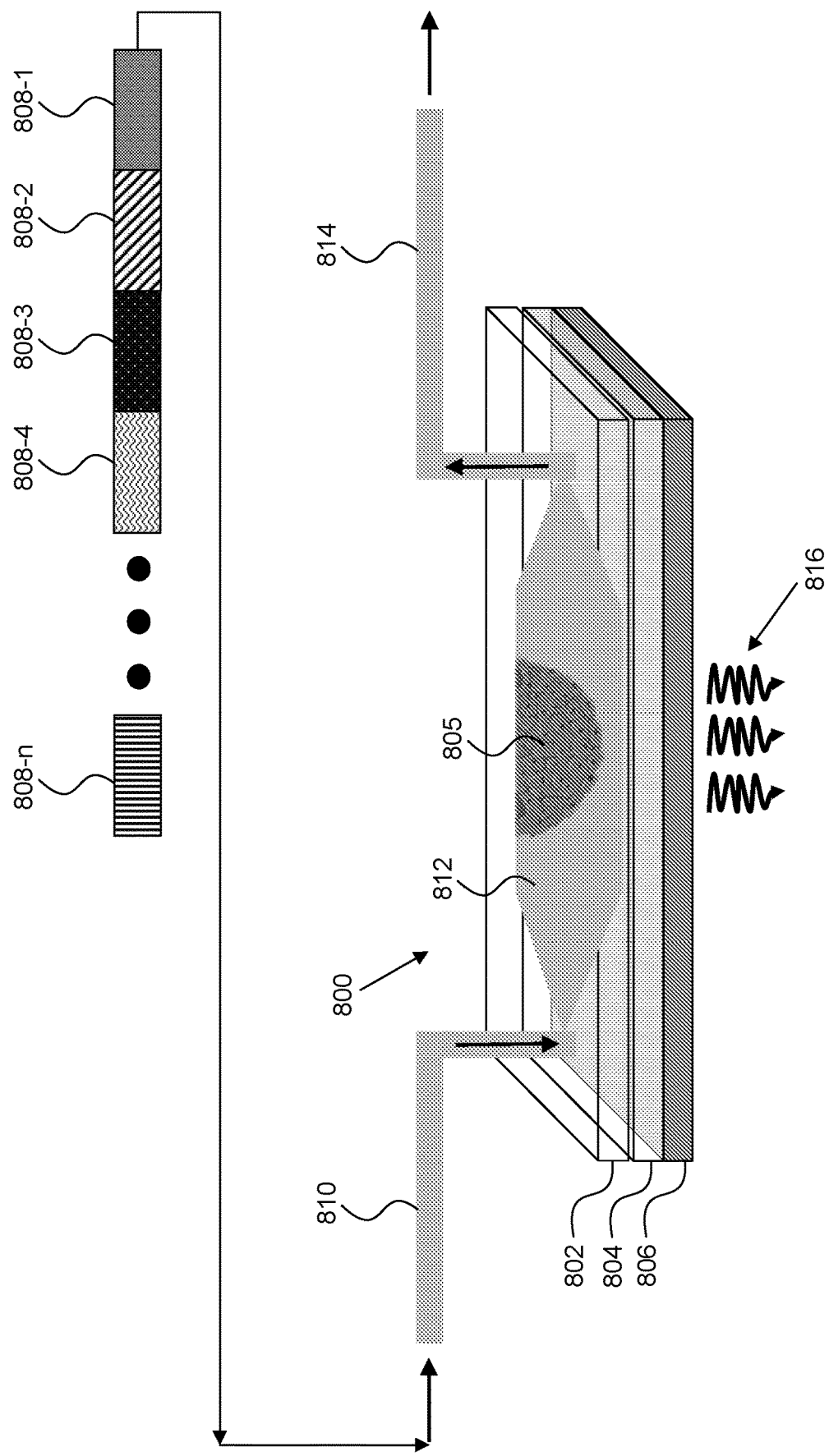

ENHANCED CYTOMETRY FOR TISSUE CHARACTERIZATION AND SCREENING

BACKGROUND

Field

Embodiments of the invention relate to imaging systems and methods, and more particularly imaging systems that facilitate analysis and characterization of biological samples, including cells and tissues.

Background

The ability to probe and characterize the expression of molecules on the surface of a cell, whether by itself or in the context of a tissue, has been vital to researchers' abilities to dissect the molecular mechanisms underlying human biology and to monitor changes associated with pathology and therapeutic intervention. In these analyses, it is important to gather information both about the type and number of molecules expressed on the cell surface, as well as the spatial relationships among cells with different expression profiles. For example, in the context of cancer, spatial information can provide clues as to which cells are attracting an immune response, and which structural subgroups are particularly susceptible or resistant to therapeutics.

State-of-the-art methods for performing such characterization are subject, however, to tradeoffs among throughput, parallelization, and maintenance of spatial information. Conventional immunofluorescence (IF) and immunohistochemistry (IHC), for example, maintain the tissue in a state close to physiological representation, but is limited by the number of spectrally distinct fluorescent probes available and the number of times one can probe the tissue. As a result, one piece of tissue can only be probed for expression of 5-7 molecules of interest. Flow cytometry, on the other hand, offers the ability to probe 15-18 molecules of interest. More recent developments in the field like CyTOF (Cytometry by Time of Flight) utilize heavy metal ion tagged antibodies, which can increase the number of probed molecules to about 100. However, in both methods, analysis happens on a single cell level, meaning the original sample must be broken up—leading to loss of key spatial information. Not only this, but once an analysis has been performed, that tissue cannot be used in other downstream analyses, like RNAsequencing, that could provide parallel information.

BRIEF SUMMARY

In the embodiments presented herein, a new imaging technique is presented to deliver a characterization method that maintains spatial information, characterizes a large piece of tissue at the same time, is theoretically unlimited in the number of surface molecules that can be probed, and preserves the integrity of the sample for downstream analyses.

In an embodiment, an optical imaging system includes a frame designed to provide mechanical coupling between a first stage and a second stage, a sample holding region located on the first stage, a lens arrangement, and a sensor array. The lens arrangement is disposed between the first stage and the second stage and is designed to receive light from a sample at the sample holding region on the first stage. The lens arrangement has a numerical aperture less than 0.1. The sensor array is coupled to the second stage and is designed to receive light passing through the lens arrangement.

In another embodiment, a method of capturing fluorescent images of a sample includes disposing the sample over a sample holding region on a stage, and disposing a substrate comprising a plurality of microfluidic channels over the sample. The method also includes flowing a solution through the plurality of microfluidic channels, such that the solution contacts the sample, and receiving light fluorescing from the sample at a lens arrangement disposed beneath the stage. The lens arrangement has a numerical aperture less than 0.1. The method also includes detecting the light fluorescing from the sample at a detector disposed optically downstream from the lens arrangement.

In another embodiment, an optical imaging system includes a frame designed to provide mechanical coupling between a first stage and a second stage, a sample holding region located on the first stage, a substrate disposed over a sample located at the sample holding region, a lens arrangement, and a sensor array. The substrate includes a plurality of microfluidic channels. The lens arrangement is disposed between the first stage and the second stage and is designed to receive light from a sample at the sample holding region on the first stage. The lens arrangement has a numerical aperture less than 0.1. The sensor array is coupled to the second stage and is designed to receive light passing through the lens arrangement.

In another embodiment, a method of detecting binding reactions includes sequentially loading probe solutions into a first channel, where each of the probe solutions includes fluorescently tagged probe molecules. The probe solutions are substantially separated from one another within the first channel. The method also includes flowing the probe solutions through the first channel and into a second channel located above a sample, such that the probe solutions contact the sample when present in the second channel. The method includes receiving light fluorescing from the fluorescently tagged probe molecules present at the sample using a lens arrangement disposed beneath the sample, and detecting the light fluorescing from the fluorescently tagged probe molecules at a detector disposed optically downstream from the lens arrangement.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 8 illustrates a testing procedure with a microfluidic device, according to an embodiment.

Figure 1:
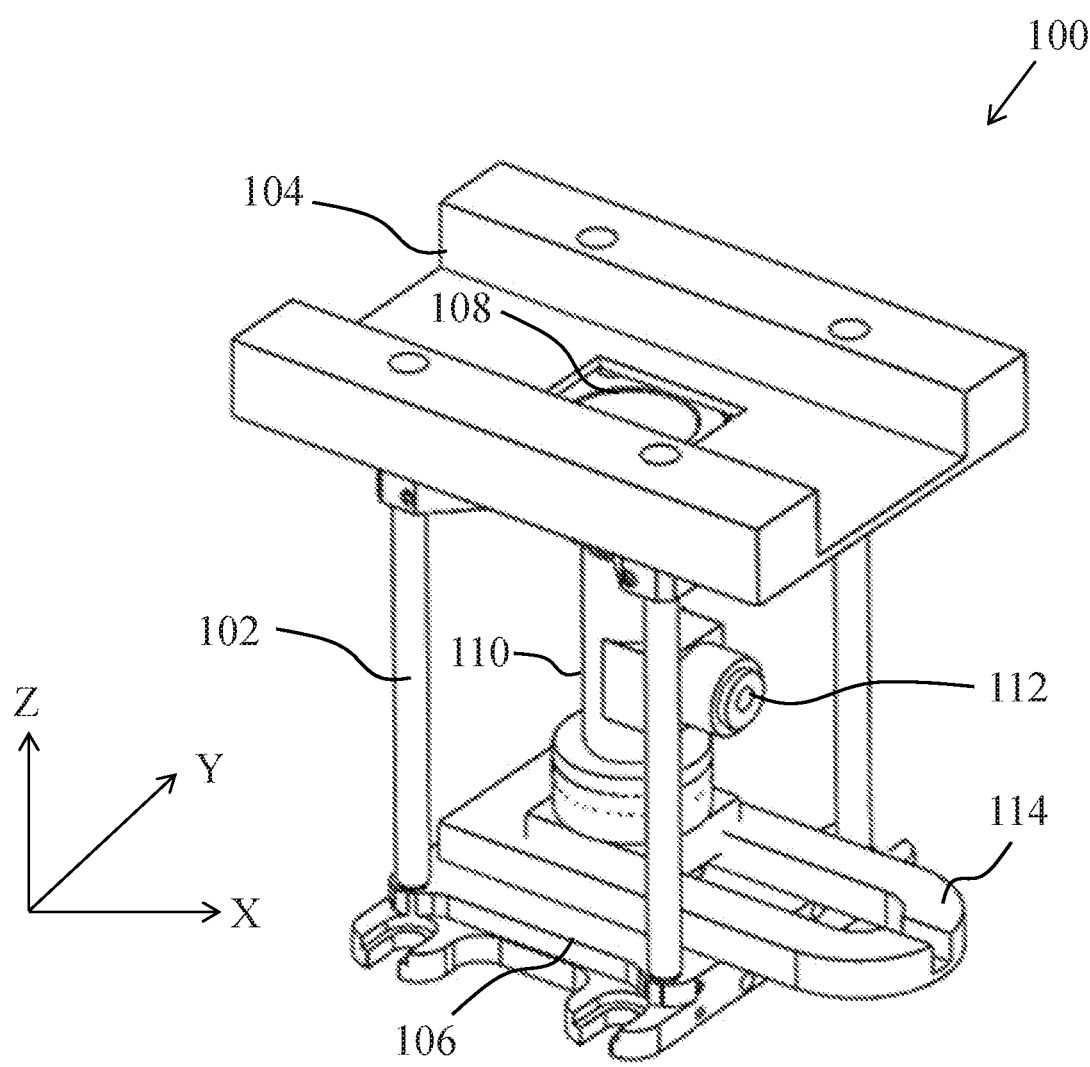
FIG. 1 illustrates a three-dimensional representation of an optical inspection system, according to an embodiment.

Embodiments of the present invention will be described with reference to the accompanying drawings. It is to be understood that the drawings are not drawn to scale and any specific geometric shapes or dimensions used in the drawings are used only to provide example embodiments of the invention.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention may also be employed in a variety of applications and is not limited to any one particular application.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Conventional microscopic imaging techniques for applications like IF and IHC sacrifice throughput for high resolution, as they employ the use of high-magnification optical systems to achieve single-cell level resolution. In these conventional systems, a tissue is operationally broken up into 30-40 smaller pieces that fit into the limited field of view of a high-resolution microscope, and each piece must be imaged by itself. As a result, one tissue, even after the laborious process of fixing, embedding, and labeling (themselves a multi-hour or multi-day process), still requires 30 minutes to 2 hours to image. After imaging, there is further image processing to be performed to reconstruct a tissue image from these 30-40 pieces.

In contrast, embodiments herein relate to an optical imaging system that may be used to capture images of a sample, where the images are characterized as having both a relatively large field of view without sacrificing resolution. As such, whole tissue samples may be imaged in the same field of view (without needing to break up the sample), while maintaining a high enough resolution for both qualitative and quantitative analysis. The samples may include disease tissue samples, or biopsy tissue samples. In some examples, the entire area of a sample fits within a single image, eliminating the need to take multiple images at different points on the sample.

FIG. 1 illustrates an optical imaging system 100, according to an embodiment. Optical imaging system 100 includes a top stage 104 supported by a frame 102. In an embodiment, frame 102 also provides mechanical coupling between top stage 104 and a bottom stage 106. Frame 102 may include any number of columns, as illustrated in FIG. 1, or may include any other structural shapes or angled members to support top stage 104 a given distance above bottom stage 106. Bottom stage 106 may provide a stable base for optical imaging system 100, and may also be coupled with detector components as will be discussed in further detail herein. In an embodiment, top stage 104 may be designed to translate along the Z-direction.

According to an embodiment, top stage 104 includes a sample holding region 108. Sample holding region 108 may be located at or near the middle of top stage 104. Sample holding region 108 may represent an opening through a bottom surface of top stage 104, such that light may pass through the opening from underneath, or from above, top stage 104. Sample holding region 108 may include a transparent block positioned over or within the opening. The transparent block may be substantially transparent to all wavelengths of light used during a given cytometry procedure. In some embodiments, sample holding region 108 may include an indentation in the bottom surface of top stage 104 that includes a bottom lip to support a glass slide or other sample-containing substrate placed in the indentation. Sample holding region 108 may also include one or more of a polarization filter, bandpass filter, or longpass filter to attenuate excitation light, but pass fluorescent light from the sample.

Positioned between first stage 104 and second stage 106 is a housing 110, according to an embodiment. Housing 110 may be coupled to second stage 106 and may house various optical elements designed to collect light from a sample placed at sample holding region 108. For example, fluorescent light generated at a sample placed at sample holding region 108 may be collected by the optical elements within housing 110.

According to an embodiment, housing 110 includes a lens arrangement that receives light from the sample. The lens arrangement is designed to have a very low numerical aperture, such that light may only enter from a small range of angles. This helps to greatly improve the resolution by removing scattered light and other sources of noise entering the lens arrangement. The low numerical aperture limits the entry of light to only light that propagates in the z-direction, or only small angles from the z-direction. In one embodiment, the numerical aperture of the lens arrangement within housing 110 is less than 0.1. In other embodiments, the numerical aperture of the lens arrangement within housing 110 is less than 0.05, less than 0.01, or less than 0.001. In an embodiment, the lens arrangement within housing 110 does not change the magnification of the collected image (i.e., the lens arrangement has a magnification of 1×). In an embodiment, the lens arrangement comprises a telecentric lens. Further discussion regarding the lens arrangement is provided with regards to FIG. 3.

In an embodiment, housing 110 includes an opening 112 along a side of housing 110. Light may be guided into opening 112 in order to provide excitation light towards a sample at sample holding region 108. For example, an optical fiber may be coupled into opening 112 to guide excitation light into opening 112. The excitation light may be used to cause the sample at sample holding region 108 to fluoresce.

In some embodiments, bottom stage 106 includes a removable component 114 that may be designed to easily slide in and out. Housing 110 may be coupled to this removable component 114 to provide a mechanism for aligning housing 110 (and consequently aligning the lens arrangement within) beneath sample holding region 108.

Figure 2:
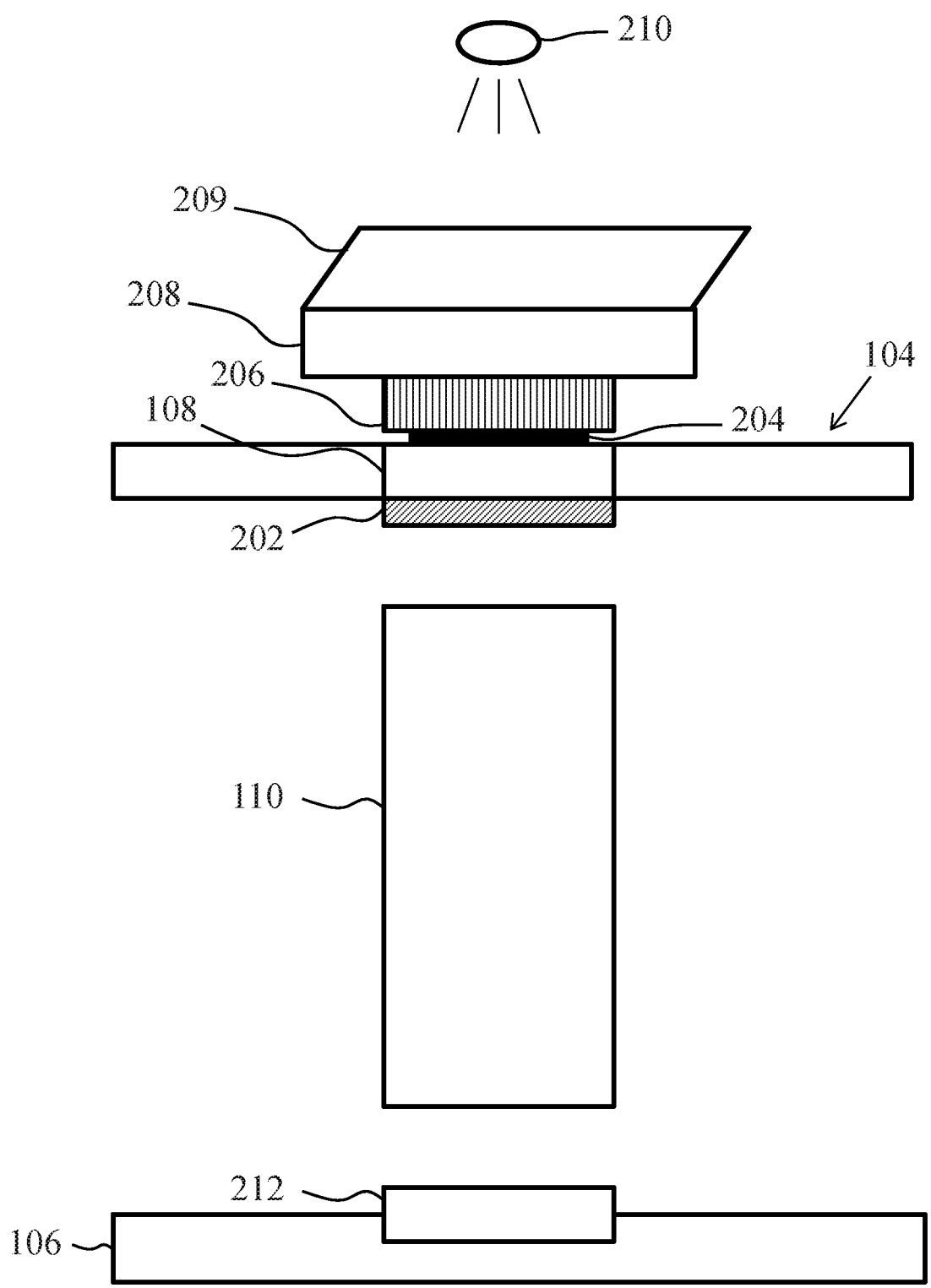
FIG. 2 illustrates a cross-section representation of an optical inspection system, according to an embodiment.

FIG. 2 illustrates a side view of various components of optical imaging system 100, according to an embodiment. In one example, sample holding region 108 supports a sample 204. Sample 204 may be placed on a glass slide or other supporting substrate before being placed over sample holding region 108. In some embodiments, sample 204 is a tissue sample.

In some embodiments, top stage 104 includes an optical filter 202 disposed beneath sample holding region 108. Optical filter 202 may include one or more of a polarization filter, bandpass filter, or longpass filter. Optical filter 202 may be included when excitation light from an illumination source 210 is directed towards sample holding region 108 from above. For example, illumination source 210 may be a blue laser or a blue LED, and the blue light excites fluorophores in sample 204 to emit higher wavelength light (such as green light). In this scenario, optical filter 202 may be used to substantially block the passage of the blue light while allowing the green light to pass. For example, a bandpass filter may only allow a band around the green light portion of the electromagnetic spectrum, e.g. about 530+/−30 nm, or a longpass filter may only allow wavelengths above a certain threshold to pass through, e.g., above 500 nm. Thus, the image of sample 204 will be primarily formed from the sample fluorescence rather than noise (e.g., the blue excitation light). Other excitation wavelengths and fluorophore wavelengths may be used with optical filter 202 adjusted accordingly to substantially block passage of the excitation light while passing the fluoresced light.

Figure 6:
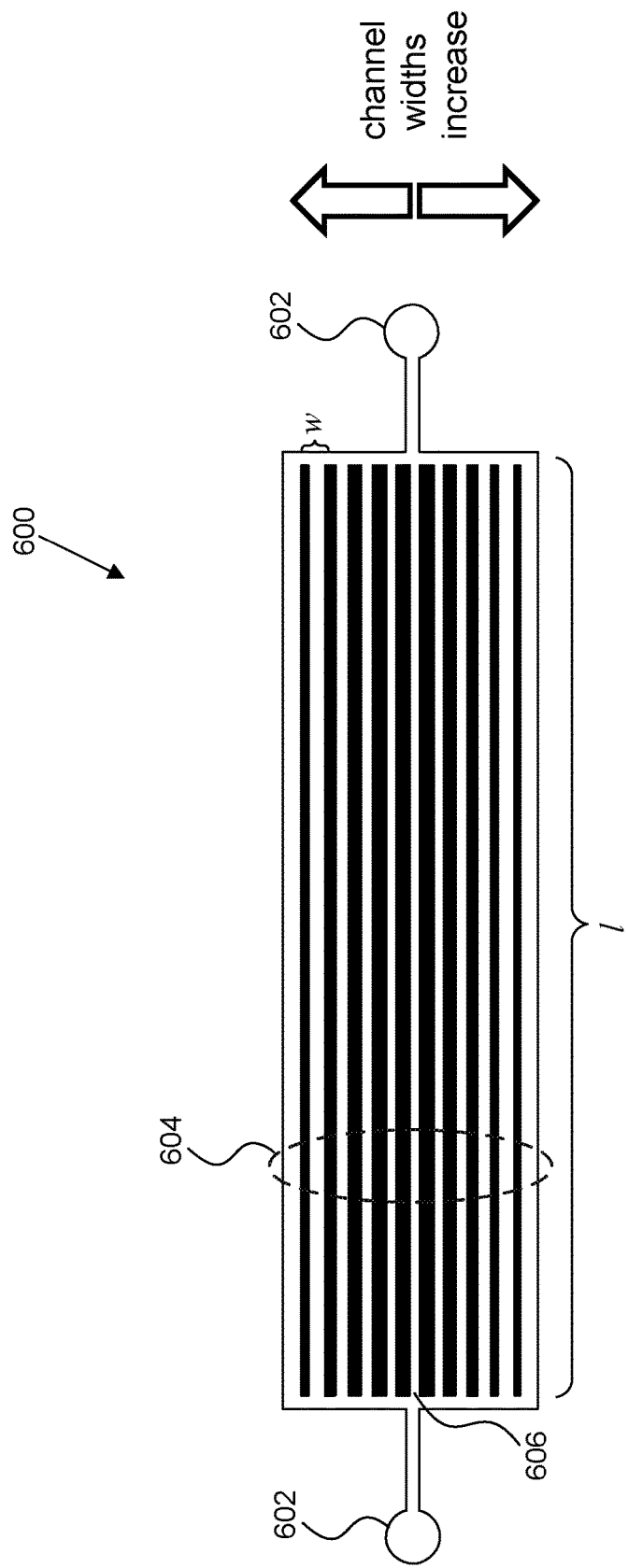
FIG. 6 illustrates a top-down view of a microfluidic device, according to an embodiment.

In an embodiment, a substrate 206 having one or more microfluidic channels is disposed over sample 204. Substrate 206 may be a glass substrate where the one or more microfluidic channels are etched within the glass substrate. In another embodiment, substrate 206 is a polymer material, such as polydimethylsiloxane (PDMS), that is molded to form the one or more microfluidic channels. Substrate 206 may also include inlet and outlet ports (not shown) to flow fluid through the one or more microfluidic channels. One example arrangement of microfluidic channels in substrate 206 is illustrated in FIG. 6.

The one or more microfluidic channels may be provided to deliver fluid over sample 204. Thus, the fluid may contact sample 204 as it flows through the one or more microfluidic channels. Tagged probe molecules (for example, tagged with various fluorophores) in a buffer solution may be delivered through the one or more microfluidic channels to bind on the surface of particular cells or cell types in sample 204. The tagged probe molecules may be cell binding agents that interact with molecules on the surface of or inside the cell. The tagged probe molecules may include antibodies, proteins, DNA, RNA, enzymes, or cells, to name a few examples. According to an embodiment, the binding that occurs between the tagged probe molecules and the sample 204 is not a covalent bond, but may be a weaker bond based on the equilibrium constant of the binding environment. Due to the weaker binding, the flow of the solution through the one or more microfluidic channels eventually washes away the bound probe molecules. This mechanism allows for multiple probe molecules to be introduced one after another over sample 204 while constantly imaging sample 204 for any binding reactions occurring between any of the tagged probe molecules and sample 204. The introduction of multiple tagged probe molecules is discussed in more detail later with reference to FIG. 7. Various wash buffers may also be delivered through the one or more microfluidic channels. In one embodiment, fluid is delivered through the one or more microfluidic channels using a pressure driven flow.

In some embodiments, substrate 206 may be plasma bonded using an oxygen plasma to a glass slide or other type of glass substrate beneath sample 204. For additional leakage protection, a top substrate 208 may be provided over substrate 206 to apply pressure downward, further sealing the one or more microfluidic channels. In some embodiments, top substrate 208 may include one or more screws (not shown) to tighten top substrate 208 downwards towards top stage 104.

An optional prism block 209 may be provided over substrate 206. Prism block 209 may be used to reduce the amount of excitation light that propagates down through sample holding region 108 towards housing 110.

Housing 110 is positioned beneath sample holding region 108 to collect light from sample 204. In an embodiment, housing 110 includes a lens arrangement and potentially other optical components to guide the received light towards a detector 212. Detector 212 may be a sensor array, such as a CMOS sensor array. In an embodiment, detector 212 may be coupled to bottom stage 106. Detector 212 may be a sensor array with a pixel size of, for example, less than 5 µm$^2$. Each pixel may have a size of, for example, about 2.2 µm×2.2 µm. The sensor array may have a total diagonal distance of, for example, less than 8 mm. In an embodiment, the field of view provided by the lens arrangement within housing 110 is roughly equal to the total footprint of the sensor array if no magnification is imposed by the lens arrangement. Accordingly, a sensor array having a diagonal footprint distance of 7.33 mm provides an image with a similar field of view of about 7.33 mm along the diagonal.

Figure 3:
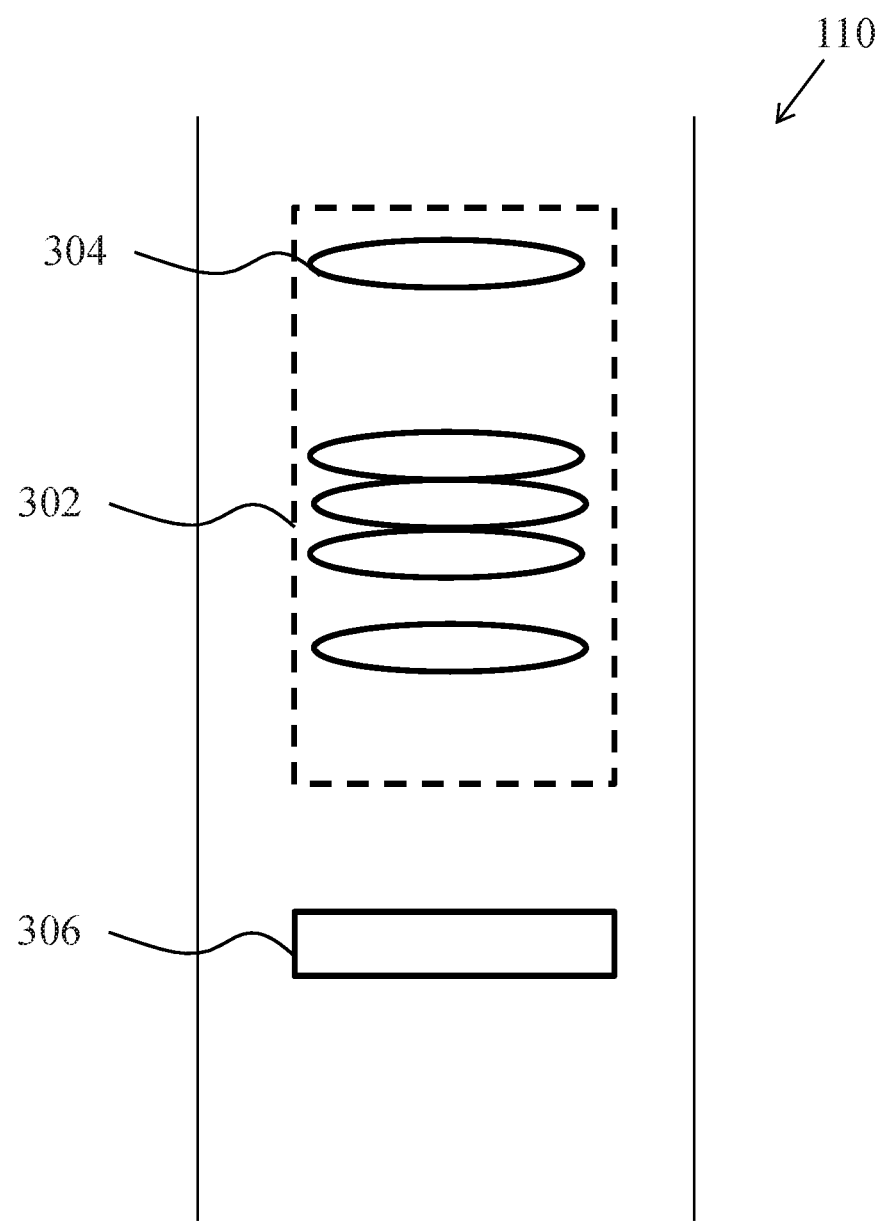
FIG. 3 illustrates a housing with a lens arrangement as used in FIG. 2, according to an embodiment.

FIG. 3 illustrates a view within housing 110 as used in the arrangement illustrated in FIG. 2, according to an embodiment. Housing 110 includes a lens arrangement 302 that includes a plurality of lenses 304. Plurality of lenses 304 may include any number and type of lens arranged such that lens arrangement 302 has a very low numerical aperture (e.g., a numerical aperture less than 0.1). In an embodiment, plurality of lenses 304 includes a telecentric lens. Examples of telecentric lenses include both bi-telecentric lenses and image-space telecentric lenses.

In some embodiments, housing 110 includes an optical filter 306. Optical filter 306 may be similar to optical filter 202 disposed beneath sample holding region 108. Accordingly, optical filter 306 may include one or more of a polarization filter, bandpass filter, or longpass filter. In some arrangements, it may not be necessary to include both optical filter 202 and optical filter 306. Thus, in some embodiments, only optical filter 306 is used without using optical filter 202, while in some other embodiments only optical filter 202 is used without using optical filter 306.

Figure 4:
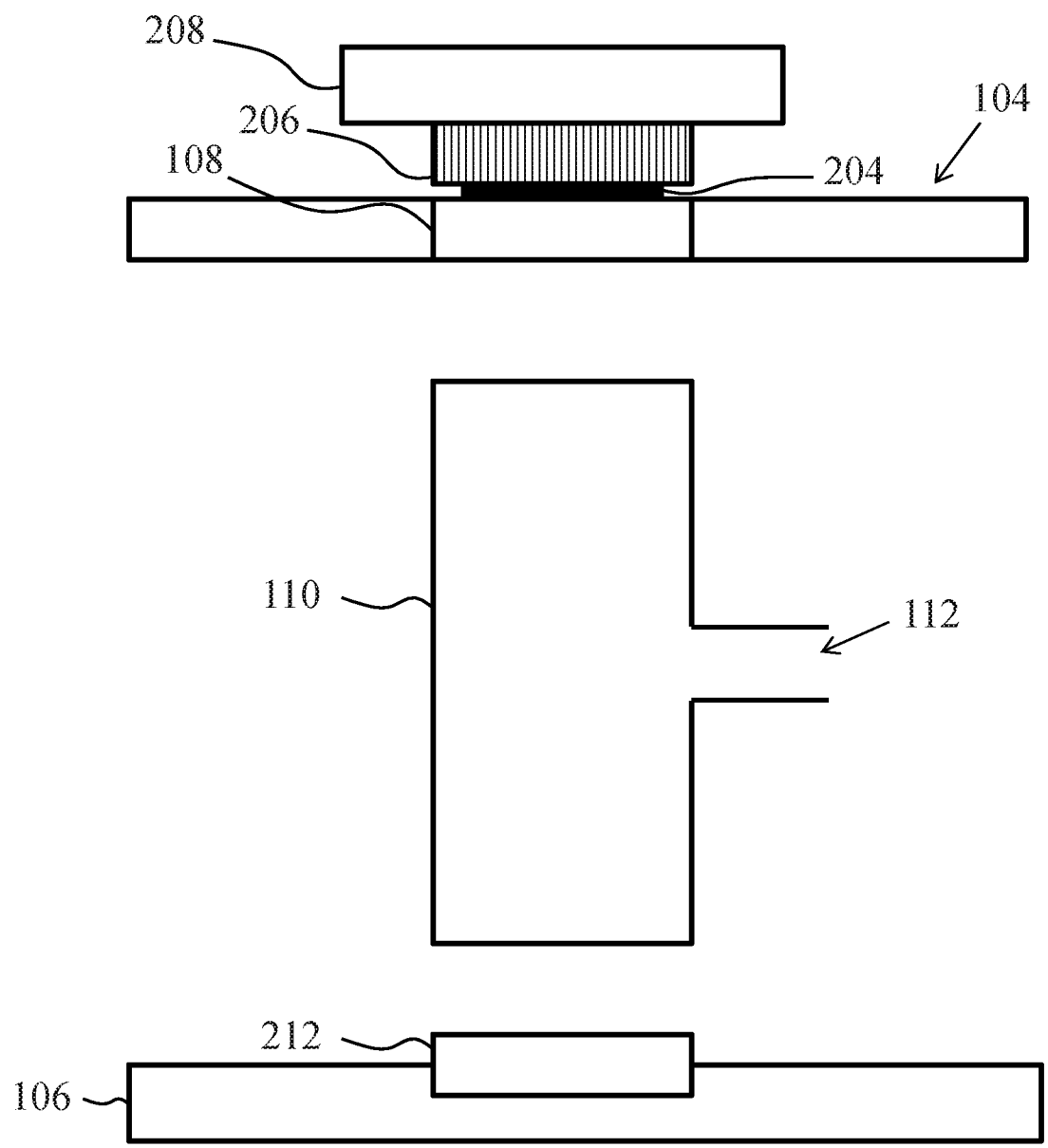
FIG. 4 illustrates a cross-section representation of an optical inspection system, according to another embodiment.

FIG. 4 illustrates another view of various components of optical imaging system 100, according to another embodiment. Many of the same elements illustrated in FIG. 2 are repeated again in FIG. 4, and thus their description is not repeated here. This embodiment uses housing 110 with an opening 112 along its side to introduce excitation light. Because excitation light is provided via opening 112, and directed towards sample holding region 108 from below, illumination source 210, prism block 209, and optical filter 202, as shown in FIG. 2, are not required in this embodiment.

Figure 5:
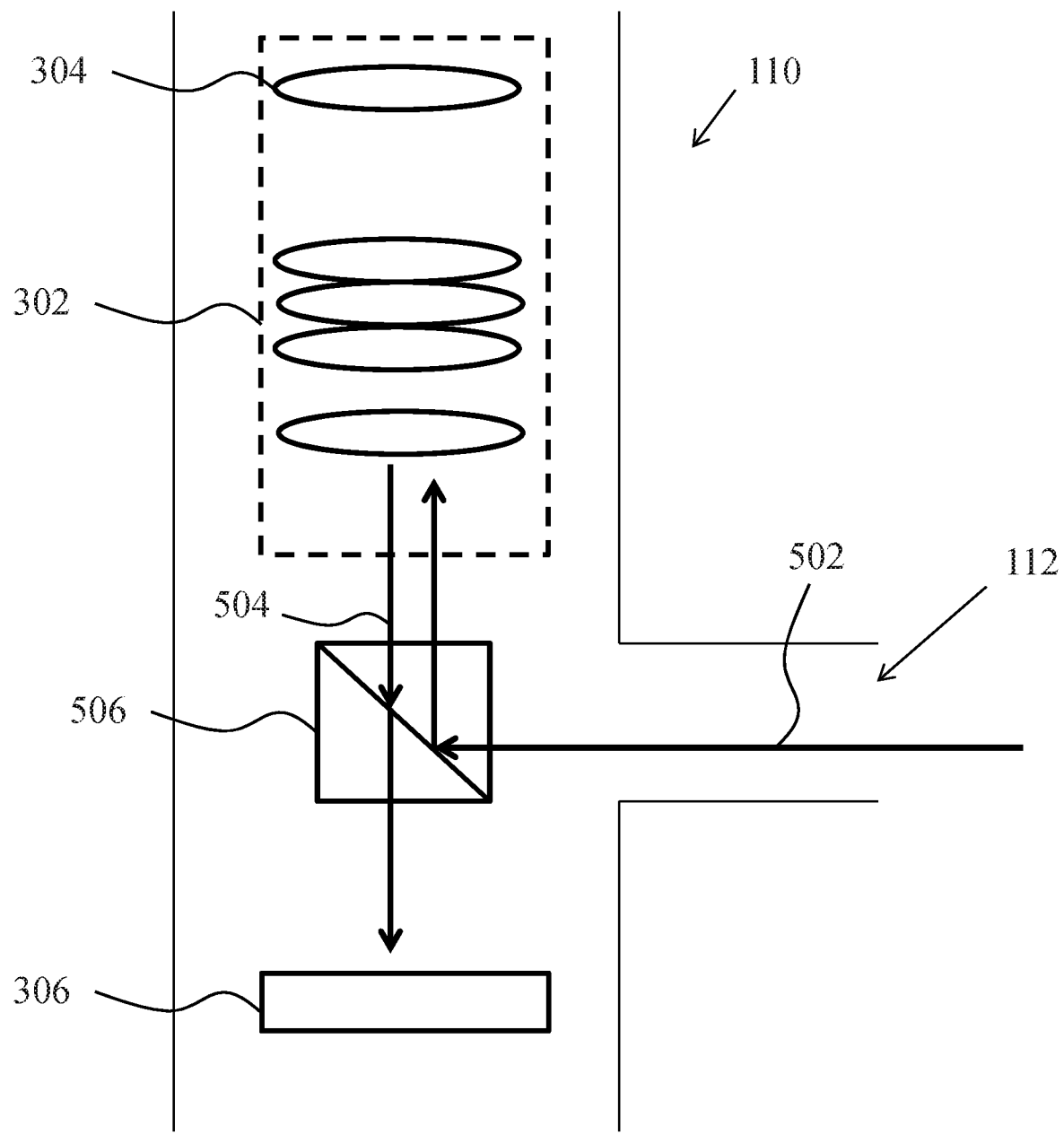
FIG. 5 illustrates a housing with a lens arrangement as used in FIG. 4, according to another embodiment.

FIG. 5 illustrates a view within housing 110 as used in the arrangement illustrated in FIG. 4, according to an embodiment. Excitation light 502 is provided through opening 112 into housing 110. Excitation light 502 is received by an angled filter 506 that is designed to reflect wavelengths below a threshold and pass through wavelengths above the threshold. Excitation light 502 is reflected from angled filter 506 and passes through lens arrangement 302 to be directed towards sample holding region 108, according to an embodiment. The light 504 received from the sample is then collected back into housing 110, through lens arrangement 302, where it passes through angled filter 506. In some embodiments, excitation light 502 and light 504 received from the sample do not interact with the same angled filter 506, and instead travel along different optical paths within housing 110.

Light 504 received from the sample may include the desired fluorescent light mixed with undesired noise from the ambient environment and/or excitation light 502. Similar to the embodiment illustrated in FIG. 3, optical filter 306 may be provided to remove any sources of noise from light 504.

FIG. 6 illustrates a top-down view of a flow cell 600 having microfluidic channels patterned therein, according to an embodiment. Flow cell 600 may be one example of substrate 206 described above with reference to FIG. 2. Flow cell 600 may be placed over a sample (e.g., a tissue sample) to deliver fluid to portions of the sample exposed beneath the microfluidic channels of flow cell 600.

According to an embodiment, flow cell 600 includes two fluidic input/output (I/O) ports 602 and a plurality of parallel microfluidic channels 604 between I/O ports 602. The plurality of parallel microfluidic channels 604 may be molded using known soft lithography techniques when flow cell 600 is a polymer material. In another example, plurality of parallel microfluidic channels 604 are etched when flow cell 600 is a more rigid material such as glass or silicon.

Fluid may be pressure-driven into one I/O port 602, such that the fluid flows through each of the plurality of microfluidic channels 604 before exiting out of the opposite I/O port 602. Each of the plurality of microfluidic channels 604 may be characterized as having a length l and a width w. According to an embodiment, the length l of each of the plurality of microfluidic channels 604 is substantially the same, while the width w of each channel increases the further the channel is from a center channel 606. For example, center channel 606 may have the smallest width w while each of the microfluidic channels at the ends has the largest width w. By having the widths of the microfluidic channels vary in this pattern, fluid will flow at substantially the same flow rate through each of the plurality of microfluidic channels 604. The widths of each channel of plurality of microfluidic channels 604 may be determined such that the same flow rate is achieved through each of the channels. This determination may depend on the viscosity of the fluid and the amount of pressure applied to the fluid as it enters I/O port 602.

The fluid may be flown between I/O ports 602 using a syringe pump or a pressurized air source. Other forms of fluid transport are possible as well, including integrated pumps, capillary action, or electro-osmotic flow. As noted above, a sample to be imaged may form the bottom surface of each of plurality of microfluidic channels 604, such that fluid flowing through plurality of microfluidic channels 604 flows directly on the sample. By controlling fluid flow through plurality of microfluidic channels 604, less analyte (compared to a non-microfluidic apparatus) is used for a given experiment with sample 204. Furthermore, other microfluidic designs utilizing multiple separated channels may be used to controllably introduce different fluids to different portions of the same sample 204.

Figure 7:
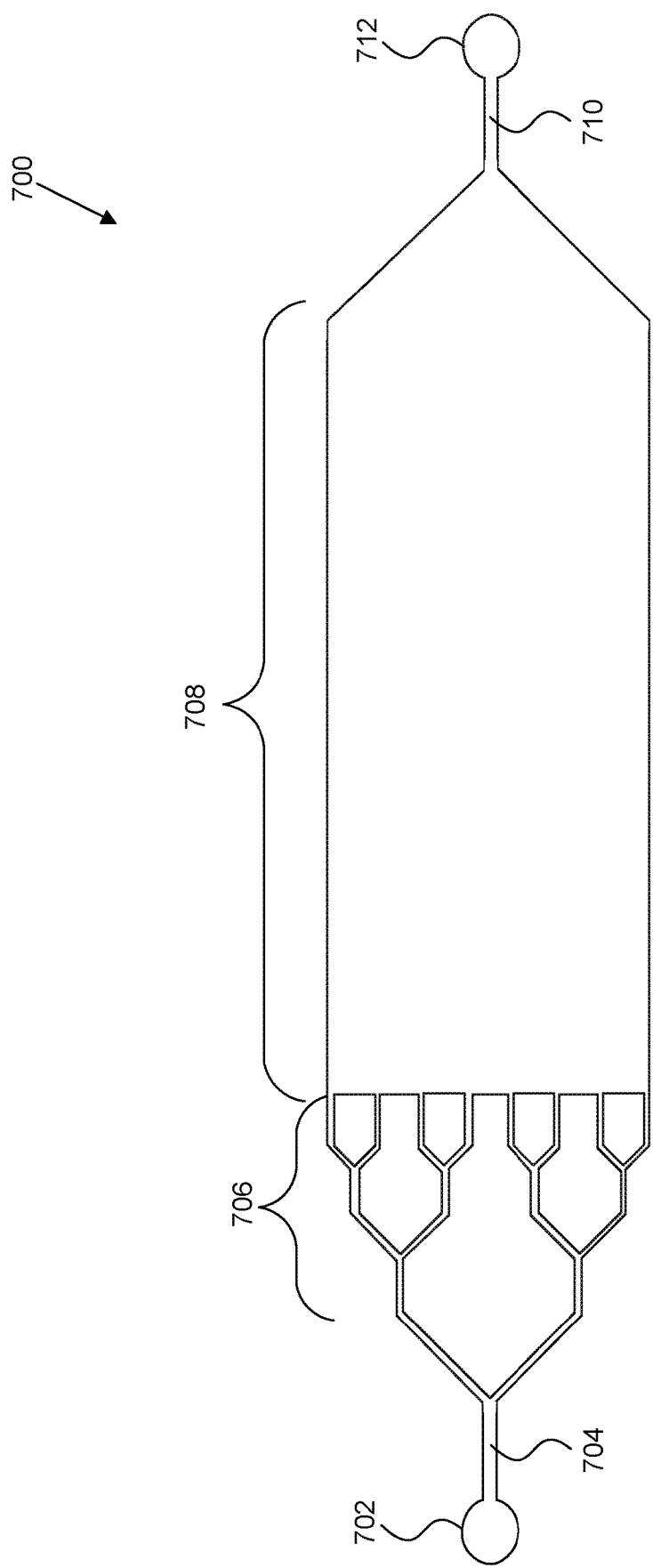
FIG. 7 illustrates a top-down view of another microfluidic device, according to an embodiment.

FIG. 7 illustrates a top-down view of another flow cell 700 having microfluidic channels patterned therein, according to an embodiment. Flow cell 700 may be one example of substrate 206 described above with reference to FIG. 2. Flow cell 700 may be placed over a sample (e.g., a tissue sample) to deliver fluid to portions of the sample exposed beneath the microfluidic channels of flow cell 700.

According to an embodiment, fluid enters flow cell 700 through an inlet port 702 and flows through an inlet channel 704 connected to inlet port 702. The fluid flows from inlet channel 704 through a branching fluidic network 706, according to an embodiment. As illustrated in FIG. 7, branching fluidic network 706 forms two branching fluidic channels at each branching point, and branches at three levels to transition from one starting channel to eight ending channels. Branching fluidic network 706 may include any total number of branching channels and any number of branching channels may be used at each branching point.

The branching channels of branching fluidic network 706 terminate into a same large fluidic channel 708, according to an embodiment. Large fluidic channel 708 may have a width that spans substantially the entire width of branching fluidic network 706. Large fluidic channel 708 may have a width between about 15 mm and 25 mm, and may have a length between about 20 mm and 30 mm. Once fluid has traversed large fluidic channel 708, it flows through an outlet channel 710 connected to a fluidic outlet 712. Branching fluidic network 706 evenly spreads the fluid flowing through inlet channel 704 along the width of large fluidic channel 708, such that the fluid flows uniformly across large fluidic channel 708, according to an embodiment.

In some embodiments, flow cell 600 or flow cell 700 may be positioned over sample 204 to deliver fluid to sample 204. Flow cell 700 may be positioned such that sample 204 is beneath large fluidic channel 708. In some embodiments, the fluid flown through the channels of either flow cell 600 or flow cell 700 includes a buffer solution containing fluorescently tagged probe molecules. The fluorescently tagged probe molecules may bind to binding partners present on or in sample 204. The binding partners may be present on or in certain cells or cell types found in sample 204. The fluorescently tagged probe molecules may include cell binding agents that interact with molecules on the surface of or inside the cell. The fluorescently tagged probe molecules may include, e.g., fluorescently tagged antibodies, proteins, DNA, RNA, cells, aptamers, or tissue fragments. Wash buffers may also be flown through the channels of either flow cell 600 or flow cell 700 to remove any non-specifically bound molecules from the channels and from the surface of sample 204.

FIG. 8 illustrates an example of flowing multiple tagged probe molecules through a fluidic channel over a tissue sample, according to some embodiments. A fluidic device 800 includes a channel layer 802 in which a fluidic channel 812 may be patterned. In one example, channel layer 802 is a glass layer and fluidic channel 812 is etched into the glass layer. In another example, channel layer 802 is a polymer layer (such as PDMS) and fluidic channel 812 is molded or patterned in the polymer layer. Channel layer 802 may have a channel design similar to that of either flow cell 600 or flow cell 700, according to some embodiments. Fluidic device 800 may also include a sample layer 804 that includes a sample 805 to be studied. Sample layer 804 may be a glass slide, or any other transparent material. Sample 805 may be a tissue sample, such as a tissue sample obtained during a biopsy of a human or animal subject. In other examples, sample 805 represents an ordered array of biological elements. For example, sample 805 may be an array of DNA sequences, RNA sequences, proteins, enzymes, ligands, antibodies, or any combination thereof. Fluidic device may also include a filter layer 806 designed to filter excitation light and pass through fluorescently emitted light 816 from the tagged probe molecules.

Fluidic channel 812 may represent any design of fluidic channel to introduce fluid over sample 805, and its illustration in FIG. 8 is not intended to be limiting. For example, fluidic channel 812 may include a single channel passing over sample 805, multiple parallel channels passing over sample 805, or other more complex configurations that could involve branching channels and fluidic valves. Fluidic channel 812 may be a microfluidic channel if fluidic channel 812 includes sub-millimeter dimensions.

According to an embodiment, multiple tagged probe molecules may be delivered one after another in a serial arrangement through fluidic channel 812 such that they each pass over sample 805. A series of probe solutions 808-1 to 808-n may be sequentially introduced via an inlet channel 810 as a series of solution plugs abutted against one another. A solution plug may be a defined volume of a given solution confined within a channel. In another example, each probe solution 808-1 to 808-n may be substantially separated from neighboring probe solutions using an air pocket or a buffer solution. In either case, the probe solutions 808-1 to 808-n are separated from one another in the inlet channel 810 or the fluidic channel 812. When probe solutions 808-1 to 808-n are sequentially introduced as a series of solution plugs, neighboring probe solutions may be substantially separated by a liquid interface. Diffusion may occur between adjacent solutions across the liquid interface, but no further mixing occurs between the solutions as they are flown through at least inlet channel 810 and fluidic channel 812, according to an embodiment. The formation of the liquid interface and lack of substantial mixing between the solutions may occur due to the small geometry of the microfluidic channels, providing laminar flow of the solution through the microfluidic channels.

Probe solutions 808-1 to 808-n may each include a population of identical probe molecules. The populations of identical probe molecules may be different between different probe solutions 808-1 to 808-n.

In the illustrated example of FIG. 8, probe solution 808-1 will be introduced first over sample 805 for a period of time based on various factors. These factors can include the dimensions of fluidic channel 812, the flow rate of the solution, and the loaded amount of probe solution 808-1. A person skilled in the art would understand how to adjust one or more of these factors to affect the time period that the probe solution is present over the sample. After probe solution 808-1 has finished flowing over sample 805, it will flow out of outlet channel 814 and be followed immediately, or after a set period of time, by probe solution 808-2, and so forth until each of probe solutions 808-1 to 808-n has been introduced over sample 805.

Figure 9B:
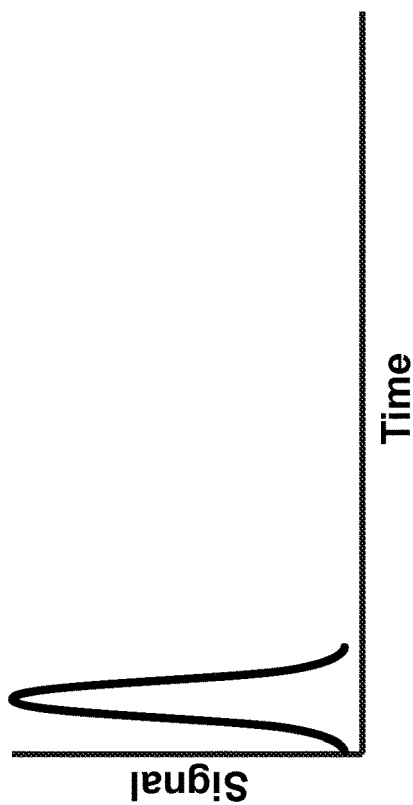
FIGS. 9A and 9B illustrate example fluorescence measurements, according to an embodiment.
Figure 9A:
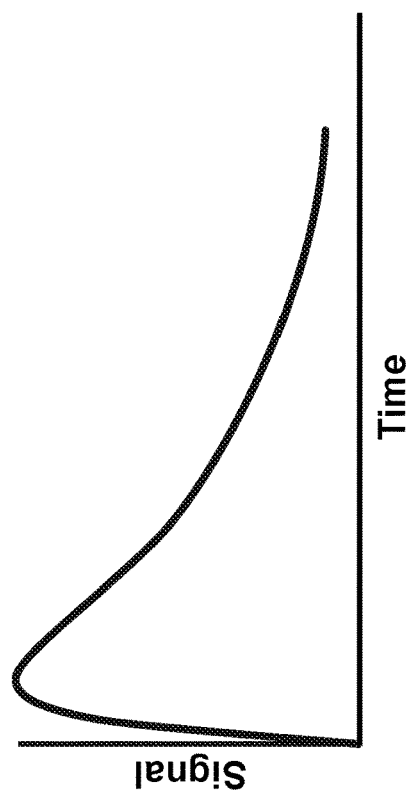

Fluorescence 816 from the tagged probe molecules is collected as the molecules flow over sample 805. FIGS. 9A and 9B illustrate example collected fluorescence signal over time for a scenario where no binding occurs (FIG. 9A) and a scenario where binding occurs (FIG. 9B). It should be noted that, for clarity, FIGS. 9A and 9B do not include the collected excitation light which will be present to some degree in the measured optical signal. Furthermore, relative peak size and width are illustrated for example purposes only and are not to be considered limiting.

When no binding occurs, the probe solution flows over sample 805 and the fluorescent tags are only briefly present over the optical collection area (since they do not bind to any part of sample 805). Thus, the resulting fluorescence signal looks like a single sharp peak centered at the peak emission wavelength of the fluorophore. However, if the probe molecules within the probe solution do exhibit some degree of binding to any part of sample 805, then the fluorescent tags will remain over the optical collection area for a longer period of time. This manifests as a more drawn-out fluorescence signal over time as illustrated in FIG. 9B. The slow decay of the collected fluorescent signal occurs due to the fluorescently tagged probe molecules being slowly washed away from their binding locations as the fluid in the channel continues to flow. The rate of decay of the fluorescent signal may be affected by the flow rate of the solution or the amount of the loaded probe solution.

In some embodiments, characteristics of the collected fluorescence signal from the probe molecules may be analyzed to determine whether or not binding occurs, which may be used to determine if a certain cell type or biological entity is present in sample 805. In some embodiments, characteristics of the collected fluorescence signal from the probe molecules may be analyzed to determine concentration or total number of target molecules (e.g., molecules that bind with the probe molecules) present in sample 805. In some embodiments, multiple emission peaks may be present simultaneously, corresponding to different fluorophores on different probe molecules.

Figure 10:
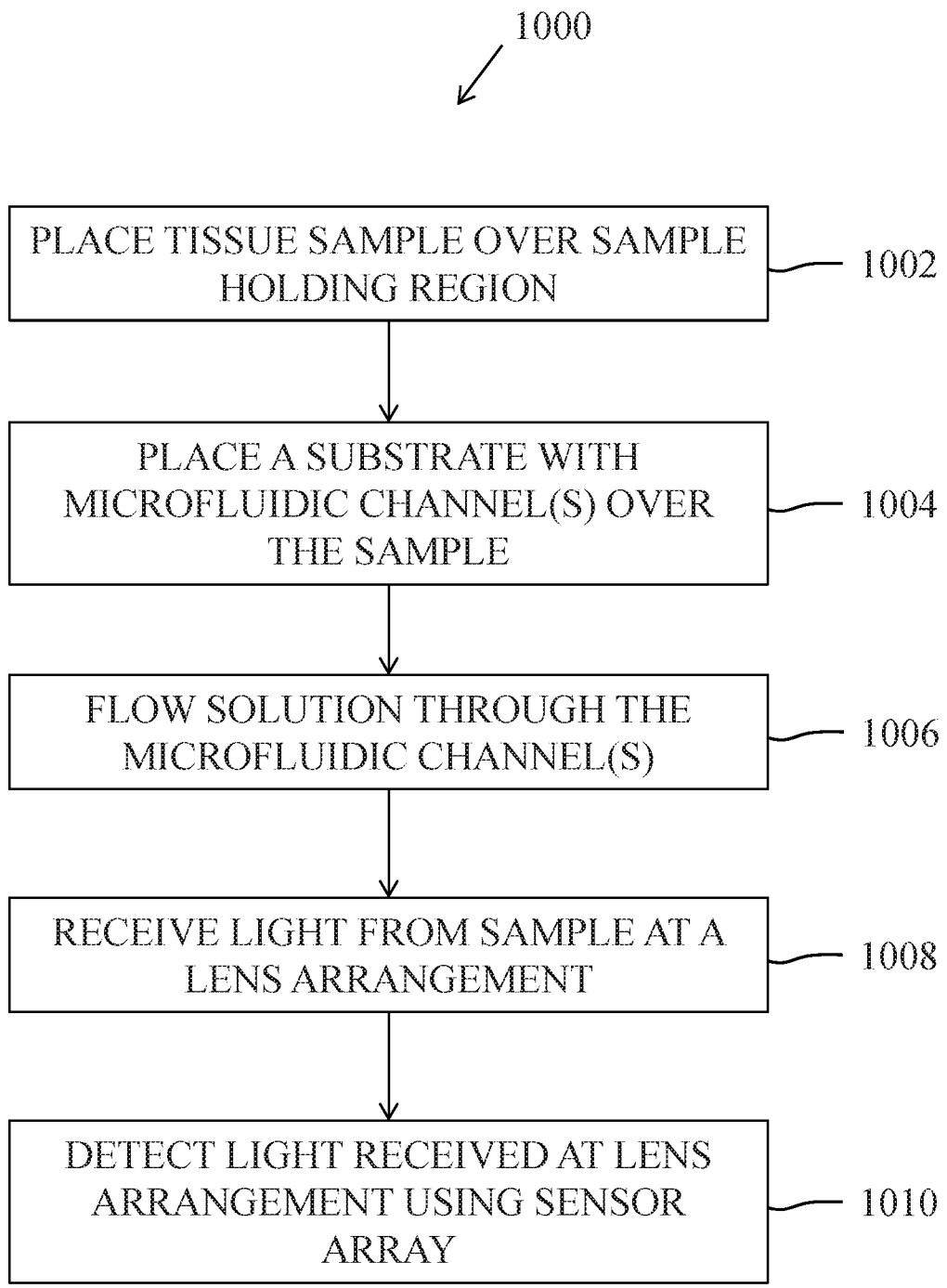
FIG. 10 illustrates a method of capturing fluorescent images of a sample, according to an embodiment.

FIG. 10 illustrates a flowchart of a method 1000 for capturing fluorescent images of a sample, according to an embodiment. Various steps of method 1000 may be performed using embodiments described herein of optical imaging system 100. It should be understood that other steps may occur between those illustrated here, but have been omitted for clarity and brevity. Such steps would involve conventional sample preparation techniques that would be well understood by a person skilled in the art.

Method 1000 begins at step 1002, where a tissue sample is placed over a sample holding region. At least a portion of the sample holding region may be transparent to substantially all wavelengths of light used during a given cytometry procedure. In some embodiments, the tissue sample is first placed on a glass slide (or similar transparent substrate) before being placed at the holding region. The glass slide may fit into an indentation at the sample holding region.

Method 1000 continues with step 1004 where a substrate with microfluidic channel(s) is placed over the sample. The substrate may be a glass substrate where the microfluidic channel(s) are etched within the glass substrate. In another embodiment, the substrate is a polymer material, such as PDMS, that is molded to form the microfluidic channel(s). Other components may also be added over the substrate. For example, a transparent prism block may be placed over the substrate and excitation light may be directed towards the prism block. The prism block may be included to reduce the amount of excitation light that is received by a downstream lens arrangement.

Method 1000 continues with step 1006 where fluid is flown through the microfluidic channel(s) in the substrate. For a substrate comprising a plurality of microfluidic channels, the fluid may be flown at substantially the same flow rate through each of a plurality of parallel microfluidic channels. The flow rate may be determined based on the geometry of the microfluidic channel(s). The fluid flow may be controlled via an applied pressure delivered by a syringe pump or pressurized air.

Method 1000 continues with step 1008, where light fluorescing from tagged probe molecules present at the sample (e.g., either bound to the sample or passing over the sample) is received at a lens arrangement positioned beneath the sample holding region, according to an embodiment. The lens arrangement may be characterized as having a very low numerical aperture, such as, for example, a numerical aperture less than 0.1. In other embodiments, the numerical aperture of the lens arrangement is less than 0.05, less than 0.01, or less than 0.001. In one example, the lens arrangement includes a telecentric lens. In some embodiments, excitation light is directed towards the sample holding region through the lens arrangement while light fluorescing from the sample is collected through the lens arrangement. The lens arrangement may be disposed within a housing.

Method 1000 continues with step 1010, where the light received at the lens arrangement is detected using a sensor array. The sensor array may include a CMOS array of detectors. In an embodiment, the field of view provided by the lens arrangement is roughly equal to the total footprint of the sensor array if no magnification is imposed by the lens arrangement. Accordingly, the physical size of the sensor array in such an embodiment is roughly equal to the field of view of the captured image. For example, a sensor array having a diagonal footprint distance of 7.33 mm provides an image with a similar field of view of about 7.33 mm along the diagonal. In some embodiments, the light received at the lens arrangement is filtered before it is received by the sensor array. The filtering may be performed by one or more of a bandpass filter, longpass filter, or polarization filter. In some embodiments, the filtering of the light is performed before the light is received by the lens arrangement.

In some embodiments, the light received by the sensor array may be used to form an image of the sample. This image may provide details of regions of the sample that are stained using tagged probe molecules, e.g., fluorescently tagged probe molecules. The image may also provide details of regions of the sample where binding occurred between the sample and the fluorescently tagged probe molecules. The intensity of the fluorescent regions in the image may be used to indicate the degree of binding that occurred. For example, an image displaying bright regions of the sample may indicate a high level of binding between the fluorescently tagged probe molecules and the sample in those bright regions.

In some embodiments, the light received at the sensor array includes any fluorescent light generated from the fluorescently tagged probe molecules at the sample. This intensity of the received fluorescent light may be used to calculate a concentration of the fluorescently tagged probe molecules present at the sample. Such studies may be performed, for example, to determine the relative concentration of certain cell types, or certain proteins on the outer surface of the cells, or any other biomolecules present in the sample. In some embodiments, the light is received from the entire sample, such that a single image can be produced of the entire sample area.

Figure 11:
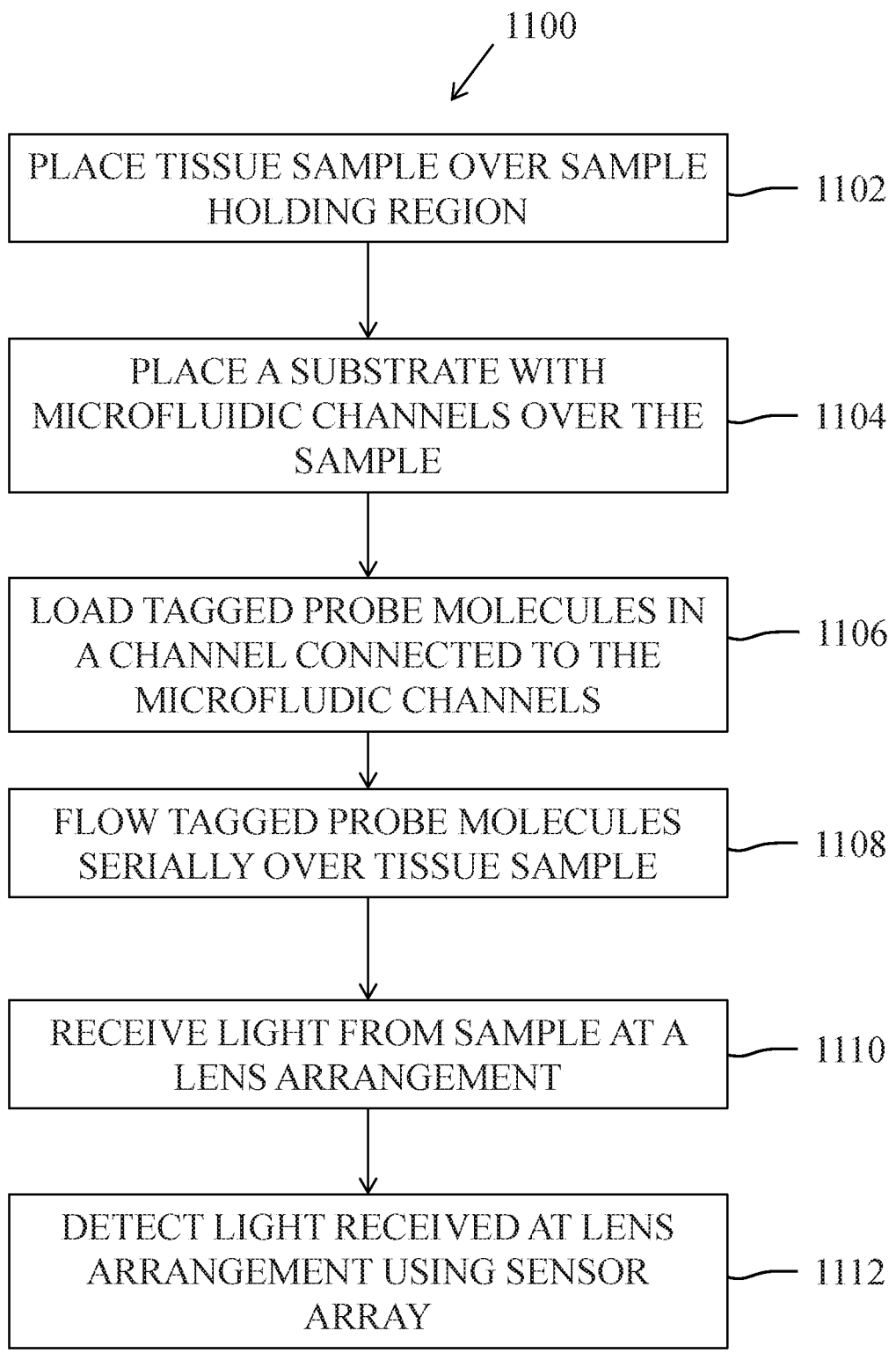
FIG. 11 illustrates another method of capturing fluorescent images of a sample, according to an embodiment.

FIG. 11 illustrates a flowchart of a method 1100 for analyzing a plurality of tagged probe molecules at high throughput, according to an embodiment. Various steps of method 1100 may be performed using embodiments described herein of optical imaging system 100 and/or fluidic device 800. It should be understood that other steps may occur between those illustrated here, but have been omitted for clarity and brevity. Such steps would involve conventional sample preparation techniques that would be well understood by a person skilled in the art.

Method 1100 begins at step 1102, where a tissue sample is placed over a sample holding region, and continues with step 1104 where a substrate having microfluidic channels is placed over the sample. These steps are similar to steps 1002 and 1004 discussed already with reference to method 1000, and thus their description is not repeated here.

Method 1100 continues with step 1106 where a series of solutions containing tagged probe molecules are loaded into a channel connected to the microfluidic channel(s). The probe solutions may be loaded sequentially into a syringe or into plastic tubing that eventually leads to the microfluidic channel(s). The probe solutions may be loaded such that each probe solution contacts neighboring probe solutions (e.g., forming a liquid interface) within the channel as they are all flown together through the channel. In another embodiment, the probe solutions may be loaded such that there is space between each probe solution in the channel. The space may be filled with air, or with another solution, such as a buffer solution.

Method 1100 continues with step 1108 where the fluorescently tagged probe molecules are flown over the tissue sample. The flow may be pressure driven, and the probe molecules may flow in a serial manner over the tissue sample. The flow rate may be adjusted to change the amount of time each probe solution is present over the tissue sample. The time a given probe solution remains over the sample may by on the order of seconds, such as, for example, between 10 and 30 seconds. High-throughput detection of multiple binding activities may be achieved by sequentially flowing any number of fluorescently tagged probe molecules across the tissue sample.

Method 1100 continues with step 1110 where light fluorescing from tagged probe molecules present at the sample is received at a lens arrangement positioned beneath the sample holding region. Method 1100 then continues with step 1112 where the light received at the lens arrangement is detected using a sensor array. These steps are similar to steps 1008 and 1010 discussed already with reference to method 1000, and thus their description is not repeated here.

Closing Remarks

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An optical imaging system, comprising:
a first stage comprising a sample holding region;
a frame configured to provide mechanical coupling between the first stage and a second stage,
wherein the first stage is configured to support a substrate comprising a plurality of microfluidic channels such that, in operation, the sample holding region holding a sample is located below the substrate supported by the first stage and a solution comprising fluorescently tagged probe molecules contacts the sample as the solution flows through the plurality of microfluidic channels;
one or more lenses disposed between the first stage and the second stage, the one or more lenses configured to receive light from the sample at the first stage, wherein an arrangement of the one or more lenses has a numerical aperture less than 0.1; and
a sensor array coupled to the second stage and configured to receive light passing through the one or more lenses, wherein the sensor array is configured to receive light passing through the one or more lenses to detect light fluorescing from the fluorescently tagged probe molecules.

2. The optical imaging system of claim 1, wherein the one or more lenses comprises a telecentric lens.

3. The optical imaging system of claim 1, further comprising a housing coupled to the second stage and configured to house the one or more lenses.

4. The optical imaging system of claim 3, wherein the housing further comprises one or more of a bandpass filter, a longpass filter, or a polarization filter.

5. The optical imaging system of claim 3, wherein the housing includes an opening along a side of the housing such that light received at the opening is directed towards the sample holding region.

6. The optical imaging system of claim 5, wherein the housing includes an angled filter configured to reflect the light received at the opening and pass the light received from the sample.

7. The optical imaging system of claim 1, wherein the one or more lenses comprises a plurality of lenses.

8. The optical imaging system of claim 1, wherein the sensor array comprises a complementary metal oxide semiconductor (CMOS) sensor array.

9. The optical imaging system of claim 1, further comprising a light source configured to provide excitation light towards the sample holding region.

10. The optical imaging system of claim 1, wherein the first stage includes one or more of a bandpass filter, a longpass filter, or a polarization filter disposed beneath the first stage sample holding region.

11. A method of capturing fluorescent images of a sample using the optical imaging system of claim 1, comprising:
disposing the sample over the sample holding region;
disposing the substrate over the sample;
flowing the solution through the plurality of microfluidic channels such that the solution contacts the sample;
receiving the light fluorescing from the fluorescently tagged probe molecules bound to the sample using the one or more lenses; and
detecting the light fluorescing from the fluorescently tagged probe molecules at the sensor array.

12. The method of claim 11, further comprising disposing a prism block over the substrate.

13. The method of claim 12, further comprising directing excitation light through the prism block towards the sample holding region.

14. The method of claim 11, wherein the flowing comprises flowing the solution at a substantially constant flow rate through the plurality of microfluidic channels.

15. The method of claim 11, wherein the detecting comprises detecting the light fluorescing from the fluorescently tagged probe molecules at a CMOS sensor array.

16. The method of claim 11, further comprising filtering light received by the one or more lenses using at least one of a bandpass filter, longpass filter, or polarization filter.

17. The method of claim 11, wherein the flowing comprises flowing the solution via an applied pressure.

18. The method of claim 11, wherein the lens arrangement comprises a telecentric lens.

19. The method of claim 11, further comprising directing excitation light through the one or more lenses towards the sample holding region.

* * * * *